(12) United States Patent
Yamauchi (10) Patent No.: US 8,785,700 B2
(45) Date of Patent: Jul. 22, 2014

(54) ALCOHOL CONCENTRATION METHOD

(75) Inventor: Kunio Yamauchi, Osaka (JP)

(73) Assignee: Nissin Foods Holdings Co., Ltd., Osaka (JP)

( * ) Notice: Subject to any disclaimer, the term of this patent is extended or adjusted under 35 U.S.C. 154(b) by 0 days.

(21) Appl. No.: 13/984,371

(22) PCT Filed: Feb. 10, 2012

(86) PCT No.: PCT/JP2012/053167
§ 371 (c)(1), (2), (4) Date: Aug. 8, 2013

(87) PCT Pub. No.: WO2012/108535
PCT Pub. Date: Aug. 16, 2012

(65) Prior Publication Data
US 2013/0345479 A1  Dec. 26, 2013

(30) Foreign Application Priority Data

Feb. 11, 2011 (JP) .................................. 2011-027981

(51) Int. Cl.
| | | |
|---|---|---|
| *C07C 29/76* | (2006.01) | |
| *C07C 29/74* | (2006.01) | |
| *C07C 31/08* | (2006.01) | |
| *C07C 31/02* | (2006.01) | |
| *C07C 31/04* | (2006.01) | |

(52) U.S. Cl.
CPC ................. *C07C 29/76* (2013.01); *C07C 29/74* (2013.01); *C07C 31/08* (2013.01); *C07C 31/02* (2013.01); *C07C 31/04* (2013.01)
USPC ........................................................ 568/913

(58) Field of Classification Search
CPC ........ C07C 29/76; C07C 29/74; C07C 31/08; C07C 31/02; C07C 31/04
See application file for complete search history.

(56) References Cited

U.S. PATENT DOCUMENTS

2012/0189790 A1   7/2012 Yamauchi et al.

FOREIGN PATENT DOCUMENTS

| JP | 4-193304 | 7/1992 |
|---|---|---|
| JP | 7-777 | 1/1995 |
| JP | 2006-88046 | 4/2006 |
| JP | 2010-235505 | 10/2010 |
| JP | 3166400 | 3/2011 |
| WO | 2011/019056 | 2/2011 |

OTHER PUBLICATIONS

International Search Report of PCT/JP2012/053167, mailing date is Apr. 24, 2012.

*Primary Examiner* — Elvis O Price
(74) *Attorney, Agent, or Firm* — Greenblum & Bernstein, P.L.C.

(57) ABSTRACT

The present invention relates to an alcohol concentration method which comprises sealing in an alcohol aqueous solution by a laminate formed by extrusion lamination of polyethylene terephthalate onto at least one surface of an air permeable film-shaped substrate; and storing the alcohol aqueous solution in the laminate for a predetermined period of time, whereby the alcohol in the alcohol aqueous solution can be concentrated easily and conveniently.

6 Claims, 3 Drawing Sheets

ALCOHOL CONCENTRATION METHOD

TECHNICAL FIELD

This invention relates to a method for concentrating alcohols, such as methanol, ethanol, propanol and butanol, in aqueous solutions containing such alcohols.

BACKGROUND ART

Ethanol or methanol is a combustible liquid and, when treated to have a higher concentration, it is increased in combustion energy. Thus, it can become an alternative fuel to gasoline, light oil or the like which is used in an internal combustion engine, etc. In recent years, moreover, moves to utilize alcohol fuels as fuels for automobiles, etc. have been speeded up, because of the limited amounts of fossil resources such as gasoline, light oil, and kerosene, and because of environmental problems. In this case as well, high concentration ethanol, for example, is needed.

As a method for concentrating ethanol, a distillation method is generally known. With this method, however, a huge amount of energy is required for heating, pressurization, etc.

As methods for concentrating ethanol at low costs, moreover, proposals have been made for an alcohol concentration method utilizing a supercritical state (Patent Document 1), and a polymer membrane separation process (Patent Document 2).

A disclosure is also made of a method which comprises reacting an alcohol in an alcohol-containing aqueous solution with a predetermined fatty acid to convert the alcohol into a hydrophobic ester compound, and hydrolyzing the hydrophobic ester compound to obtain ethanol (Patent Document 3).

PRIOR ART DOCUMENTS

Patent Documents

Patent Document 1: JP-A-4-193304
Patent Document 2: JP-A-7-777
Patent Document 3: JP-A-2010-235505

SUMMARY OF THE INVENTION

Problems to be Solved by the Invention

The methods described in the above-mentioned Patent Documents 1 and 2, however, still pose the problem of a high cost and a problem with the durability of the separation membrane. Even with the method described in the Patent Document 3, a predetermined organic solvent and a predetermined chemical are needed, and a meticulous operation is necessary, so that much time and labor are required.

The conventional methods for concentration of ethanol, as described above, have required an enormous amount of energy and certain plants. Thus, an easier and less expensive method for concentration has been desired.

Under these circumstances, the present inventor has aimed at developing a method for concentrating an alcohol in an alcohol-containing aqueous solution with greater ease.

Means for Solving the Problems

The present inventor and others investigated a method for obtaining a laminate by extrusion laminating molten polyethylene terephthalate directly onto a paper substrate, without using an anchor coating agent. When they conducted various tests using the laminate obtained by this method, they found this laminate to be utilizable for the concentration of alcohols.

That is, they found that when a container was prepared using the laminate, an alcohol-containing aqueous solution was sealed into the container to attain a sealed state, and the solution was stored in this state for a predetermined period of time, only water in the solution volatilized to concentrate ethanol.

According to the present invention, therefore, there is provided an alcohol component concentration method, including following steps of:

sealing in an alcohol-containing aqueous solution by a laminate formed by extrusion lamination of polyethylene terephthalate onto at least one surface of an air permeable film-shaped substrate; and storing the alcohol-containing aqueous solution in the laminate for a predetermined period of time.

In the alcohol component concentration method of the present invention, it is preferred that
1. the polyethylene terephthalate be homopolyethylene terephthalate;
2. the laminated surface in the laminate formed by extrusion laminating the polyethylene terephthalate be heat sealable;
3. the substrate be paper, a nonwoven fabric, or a mesh;
4. the inherent viscosity of the polyethylene terephthalate be 0.72 to 0.88 dL/g; and
5. the extrusion laminating be performed by a laminating method which comprises extruding molten polyethylene terephthalate through a die, such as a T-die, for lamination, wherein an air gap from the opening of the die up to the supporting substrate is 25 cm or less.

According to the present invention, there is also provided a laminate for use in the alcohol component concentration method, wherein the laminate is formed by extrusion laminating polyethylene terephthalate onto at least one surface of an air permeable film-shaped substrate.

Effects of the Invention

According to the alcohol component concentration method of the present invention, even an alcohol-containing aqueous solution of a low concentration can be concentrated to a high concentration by a simple and convenient method, without the need for great energy, chemicals or plants. Thus, the method of the invention can contribute to the utilization of alcohol fuels.

According to the laminate utilized in the alcohol component concentration method of the present invention, the alcohol aqueous solution can be easily sealed in, because the laminate has heat sealability.

MODE FOR CARRYING OUT THE INVENTION

Embodiments of the present invention will be described below.

(Polyethylene Terephthalate)

In the laminate used in the alcohol component concentration method of the present invention, it is an important feature that polyethylene terephthalate is directly coated on at least one surface of an air permeable film-shaped substrate.

The polyethylene terephthalate in the present invention consists essentially of a polyester which is formed by condensation polymerization of ethylene glycol as a diol component and terephthalic acid as a dicarboxylic acid component, and which has ester bonds connected together. The formation of the ester bonds can be performed even by an ester interchange reaction with dimethyl terephthalate.

In the laminate used in the present invention, it is preferred to use homopolyethylene terephthalate as the polyethylene terephthalate. This homopolyethylene terephthalate refers to general-purpose polyethylene terephthalate which is formed by polycondensation of ethylene glycol as a diol component and terephthalic acid as a dicarboxylic acid component, and which does not positively contain other component. The homopolyethylene terephthalate is not meant to exclude impurities which are formed as by-products during preparation of polyethylene terephthalate.

That is, "home" in the homopolyethylene terephthalate is to the effect that a special polyester resin such as a copolyester resin or a blend resin is excluded. For example, Japanese Patent No. 3749000 names examples of special polyester resins.

It goes without saying that the "homopolyethylene terephthalate" as referred to in the present invention also includes one which intentionally incorporates a trace amount of a third component in regard to the technical scope of the present invention.

It is important in terms of film-forming properties that the inherent viscosity (IV) of the homopolyethylene terephthalate used in the laminate of the present invention be in the range of 0.72 to 0.88 dL/g, particularly 0.80 to 0.83 dL/g. If the inherent viscosity is lower than this range, the film-forming properties will be poor. If the inherent viscosity is higher than this range, poor extrudability will arise. Further, the homopolyethylene terephthalate used in the laminate of the present invention can incorporate compounding agents for film publicly known per se, for example, anti-blocking agents, antistatic agents, lubricants, antioxidants, and ultraviolet absorbers, in accordance with publicly known formulations.

(Air Permeable Film-Shaped Substrate)

In the present invention, the alcohol is concentrated using the laminate formed by extrusion laminating the polyethylene terephthalate onto the air permeable film-shaped substrate. By laminating polyethylene terephthalate to the film-shaped substrate, the substrate serves as a protective substrate for the polyethylene terephthalate layer, thus preventing damage or the like caused to the layer, and facilitating its handling.

In the present invention, the film-shaped substrate needs to have air permeability in order to seal the alcohol-containing solution with the laminate and volatilize water contained in the alcohol.

Concrete examples of the air permeable film-shaped substrate in the present invention include, but are not limited to, paper, cloth and a nonwoven fabric.

In the case of paper as the film-shaped substrate used in the laminate, paperboards conventionally used in paper containers can all be used, and various forms of them can be adopted according to uses. For example, ivory board, cup stock base paper, Manila board, boxboard, and synthetic paper can also be used, although these are not limitative.

The basis weight of the base paper is not limited, but preferably, it is generally in the range of 180 to 500 g/m$^2$.

If the basis weight is less than this range, the mechanical strength of the resulting container may be inferior to that obtained using the above range. If the basis weight is greater than the above range, on the other hand, the resulting container is so heavy that its handleability and economy may be poor and its formability may be inferior as compared with the basis weight being in the range.

To enhance the wettability of the surface of the paper substrate and improve its adhesion to polyethylene terephthalate, the paper substrate may be subjected to surface treatment such as corona discharge treatment, flame treatment, plasma processing, or ozonization.

For the nonwoven fabric or the mesh, various types can be used. For example, spunbonded polyester, or polyolefin nonwoven fabrics or meshes are named.

(Laminate)

In the laminate used in the alcohol concentration method of the present invention, a coating layer comprising the above-mentioned polyethylene terephthalate (may hereinafter be referred to simply as "PET") is formed on at least one surface of the film-shaped substrate. Preferably, the PET layers are coated on both surfaces of the film-shaped substrate.

The thickness of the PET layer cannot simply be defined depending on the uses of the laminate, the shape of a container formed from the laminate, and so on. However, from the aspect of film-forming properties, heat resistance, water resistance, aroma barrier properties, or heat-sealability, its thickness is preferably in the range of 10 to 60 μm. A more preferred range is 12 to 50 μm.

Within any such range, sufficient heat sealability can be ensured in relation to heat sealing to be described later, and the degree of sealing can be adjusted.

For the laminate comprising polyethylene terephthalate laminated therein, which is utilized in the present invention, water vapor permeability needs to be maintained. Thus, a layer with high water vapor barrier properties, such as an aluminum foil or an olefin resin layer, cannot be provided.

(Heat Sealability)

The laminate formed by extrusion lamination of polyethylene terephthalate, which is utilized in the present invention, preferably has heat sealability. That is, it is necessary in the present invention to accommodate an alcohol aqueous solution in the above laminate, then seal the laminate, and store the alcohol aqueous solution in the sealed laminate, as will be described later.

In order to seal the laminate, with the polyethylene terephthalate surface in contact with the alcohol aqueous solution, it is permissible to heat seal the polyethylene terephthalate surfaces to each other, whereby a sealed state can be easily achieved. By setting conditions depending on the manufacturing method to be described later, the heat sealability of the laminate in the present invention can be maintained.

(Method for Producing Laminate)

In the method for producing the laminate used in the present invention, it is not that a stretched polyethylene terephthalate film is bonded to the film-shaped substrate with the use of an adhesive or the like. Instead, polyethylene terephthalate is melt extruded, and coated (laminated) directly onto the surface of the film-shaped substrate.

In this case, laminating can be performed, even when no anchor coating agent is coated on the surface of the film-shaped substrate onto which the polyethylene terephthalate is to be laminated.

In laminating a molten resin form of polyethylene terephthalate onto the film-shaped substrate by extrusion coating in the production of the laminate utilized in the present invention, it is important to select processing conditions.

Particularly, the distance between the lip opening of the die and the film-shaped substrate is of importance. It is preferred to set the distance from the lip opening of the die to the film-shaped substrate (i.e., air gap) at 25 cm or less, preferably in the range of 5 to 20 cm.

Moreover, the extrusion temperature of the molten resin extruded from the extruder is preferably set at a value in the range of nearly Tm+25° C. or higher, but lower than Tm+70° C., based on the melting point (Tm) of the polyethylene terephthalate used.

Furthermore, the extrusion pressure during extrusion is preferably set at 3.5 to 6.5 MPa, particularly 4.0 to 6.0 MPa.

Preferably, the deviation of the actual measured temperature from each temperature setting should be small. Pressure adjustment as well should preferably be made precisely.

By setting the parameters in the above ranges, the occurrence of film shaking can be suppressed, and the laminate excellent in the uniformity of the film thickness or excellent in the adhesion of the coating can be produced easily. These facts will become clear also from the results of the Examples to be described later.

That is, as will be clear from the results of the Examples to be described later, if the air gap is larger than 25 cm, selvage shaking, namely, bilateral shaking of both edges (selvages) of the film, occurs in a width of 4 mm or more, and the range of fluctuations in the film thickness is ±20% or more of the desired thickness, so that a film (PET layer) of a uniform thickness is difficult to form (Comparative Example 1, Table 1). Moreover, the heat-sealability is also insufficient (Comparative Example 1, Table 4).

If the extrusion temperature of polyethylene terephthalate during melt extrusion deviates from the range of Tm+25° C. to Tm+70° C., a coating of a uniform film thickness is difficult to form, and the resulting film is clearly inferior in selvage shaking and adhesion to the one fulfilling the above range (Comparative Examples 2 and 3, Table 2). If the extrusion pressure deviates from the range of 3.5 to 6.5 MPa, moreover, the resulting film is clearly unsatisfactory in terms of selvage shaking and film thickness uniformity in comparison with that meeting the above range (Comparative Examples 4 and 5, Table 3).

In the production method that satisfies all of the above-mentioned conditions, by contrast, it is clear that the width of selvage shaking is restricted to less than 4 mm, the range of fluctuations in the film thickness is as narrow as less than ±20% of the desired film thickness, and the adhesion is excellent (Examples 1 to 18).

Figure 1:
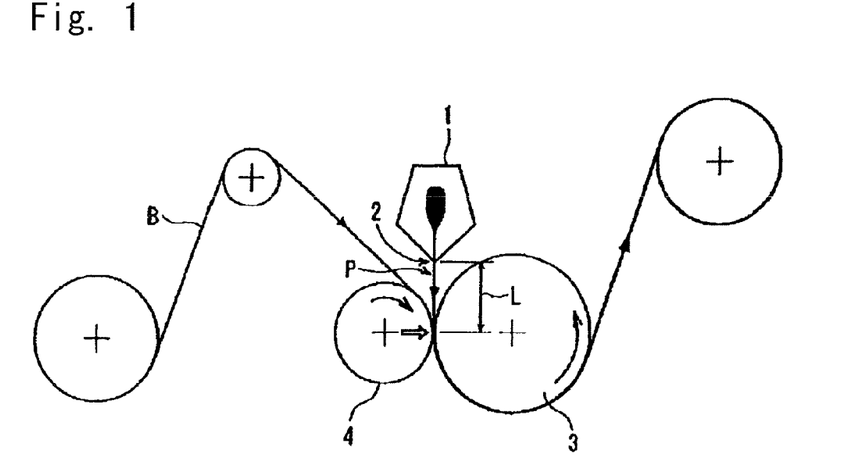
FIG. 1 is a schematic view showing the layout of an example of an apparatus used in the method for producing the laminate of the present invention.

FIG. 1 is a schematic view of an example of an apparatus used in the method for producing the laminate of the present invention. Polyethylene terephthalate is melt-kneaded by an extruder (not shown), and extruded as a molten resin film P through lips 2 of a T-die 1 onto the surface of a paper substrate B. Then, the film-substrate combination is nipped between a chill roll 3 and a pressure roll 4, whereby the laminate of the present invention is produced. The air gap is expressed as the distance L from the lips 2 of the T-die to the surface of the paper substrate B.

In the present invention, after the PET molten resin film P is extruded onto the film-shaped substrate B, the resulting composite is nipped between the chill roll 3 and the pressure roll 4, as stated above. It is desirable on this occasion that the PET layer be quenched by the chill roll to suppress the crystallization of the polyethylene terephthalate. This enables the heat-sealability of the PET layer to be ensured. The surface temperature of the chill roll is preferably in the range of 10 to 35° C., although it is not limited.

It is also important to maintain the extrusion pressure of the molten resin film at a constant value, and it is additionally desirable to provide a gear pump between the extruder and the die, although this is not illustrated.

As the die for extruding the polyethylene terephthalate, use can be made of a die generally used for extrusion coating of resin. Preferably, the opening width of the die lips is in the range of 0.4 to 1.4 mm, and the width of the die is in the range of 90 to 180 cm. Under the conditions of the present invention, moreover, lamination at a line speed of 50 to 100 m/min is preferred in terms of a uniform film thickness and the adhesion of the PET layer.

(Alcohol-Containing Aqueous Solution)

The alcohol-containing aqueous solution as referred to in the present invention (may herein be simply called "alcohol aqueous solution") refers to a solution containing at least water and an alcohol component. The type of the alcohol is not limited, but ethanol, methanol, propanol and butanol are named as examples.

Any such alcohol aqueous solution (for example, an ethanol aqueous solution) needs to be concentrated, particularly as bioethanol has found widespread use in recent years. According to methods for obtaining ethanol by fermentation with the use of grain or the like as a raw material, the concentration of alcohol is generally a low concentration of the order of about 10%. With the concentration method of the present invention, concentration is possible even from such a crude ethanol aqueous solution.

Furthermore, concentration from various waste liquors containing ethanol is also possible. If large amounts of impurities are contained, it is needless to say that a purification steps, such as filtration or centrifugation, may be added if desired.

(Concentration of Alcohol)

The concentration of alcohol in an alcohol aqueous solution, the object to be concentrated by the method of the present invention, is not limited. That is, only if the alcohol aqueous solution contains ethanol even in a concentration of several percent, it can be concentrated.

Nor is the ethanol concentration after the concentrating operation limited, but if a long storage period is set, concentrating to an alcohol concentration of up to 99% or higher is possible.

The alcohol aqueous solution poses no problem, even if it contains impurities during concentration as well as before concentration. If the impurities are solids, in particular, they can be removed by means, such as filtration or decantation, either before concentration or during concentration.

If salts, protein, etc. are contained in the alcohol aqueous solution, concentrating the alcohol aqueous solution to a certain extent may precipitate them as solids. By separating them and continuing concentration, therefore, the impurities can be decreased.

(Sealing-in of Alcohol Aqueous Solution)

In the present invention, the polyethylene terephthalate layer of the laminate used has heat sealability. Thus, the alcohol aqueous solution can be sealed in by forming the inner surface of an enclosure from polyethylene terephthalate, accommodating the alcohol aqueous solution inside the enclosure, and then heat sealing the polyethylene terephthalate layer surfaces of the enclosure to each other.

Since the alcohol aqueous solution can be sealed in relatively easily in the above manner, the sealing state can be adjusted with ease.

Concretely, a container is prepared using the laminate, and heat is applied to the surfaces of polyethylene terephthalate, whereby the opening of the container prepared from the laminate can be sealed.

The temperature of heat sealing is not specified, but may generally be of the order of 160° C. or higher. An impulse sealer or the like can be used for heat sealing.

Apart from the above method of sealing by heat sealing or the like using the laminate, a method is also available which comprises putting an alcohol aqueous solution, an object to be concentrated, into a rigid container such as a metal or plastic container, applying the laminate of the present invention, as a lid, to an open upper part of the container, and heat-sealing the opening of the container and the polyethylene terephthalate portion of the laminate. Since the present invention involves polyethylene terephthalate, in particular, it is preferred to use a plastic container made of polyethylene terephthalate.

Alternatively, it is advisable to accommodate an alcohol aqueous solution in a bag formed from a material such as polyethylene terephthalate, and then heat-seal an opening of the bag with the laminate of the present invention.

(Storage Conditions, Storage Temperature and Storage Period)

In the present invention, the storage conditions for the container accommodating and sealing in the alcohol aqueous solution are not limited, but the preferred storage temperature is of the order of normal temperature to 70° C. Particularly, a temperature of the order of 30 to 60° C. is more preferred. The higher the storage temperature, the shorter time is required for concentration.

In the present invention, concentration can take place, with the container being simply stored (allowed to stand) under the above temperature conditions. Hence, any other redundant operation or the like is unnecessary.

After storage for a predetermined period, the container is unsealed, and concentrated ethanol can be recovered.

EXAMPLES

Examples of production of the laminate having polyethylene terephthalate laminated to the film-shaped substrate, and Examples of ethanol concentration using the laminate will be shown below as Examples of the present invention.

1. Preparation of Polyethylene Terephthalate Laminate

Example 1

An extrusion laminator was adjusted such that an air gap with respect to a die (width: about 110 cm) having a lip opening width adjusted to 0.8 mm (air gap=the distance from the lip opening of a T-die to a cup stock base paper to be coated) would be 10 cm. Homopolyethylene terephthalate at an extrusion temperature of 300° C. was extruded from the die at an extrusion pressure of 6.0 MPa, and coated on a cup stock base paper (corona discharge treated; basis weight 320 g/m$^2$). The homopolyethylene terephthalate used in Examples 1 to 14 and Comparative Examples 1 to 5 was one having an inherent viscosity of 0.83 dL/g and a melting point of 250° C. (NOVAPEX BK6180, produced by Mitsubishi Chemical Corp.).

The coating thickness of the homo-PET was 25 and the coating line speed was 65 m/min. Simultaneously with the coating on the base paper, the coated base paper was passed between a chill roll (surface temperature: 22° C.) and a rubber roll to complete a laminate. In connection with these steps, the state of the extruded laminate was evaluated. The results are shown in Table 1.

Examples 2 to 5 and Comparative Example 1

The same procedure as in Example 1 was performed, except that the air gap was set at the values shown in Table 1. The state of the extruded laminate was evaluated. The results are shown in Table 1.

Example 6

The same procedure as in Example 1 was performed, except that the air gap was set at 15 cm and that the extrusion temperature of the homopolyethylene terephthalate was set at 280° C. The state of the extruded laminate was evaluated. The results are shown in Table 2.

Examples 7 to 9 and Comparative Examples 2 to 3

The same procedure as in Example 6 was performed, except that the extrusion temperature of the homopolyethylene terephthalate was set at the temperatures shown in Table 2. The state of the extruded laminate was evaluated. The results are shown in Table 2.

Example 10

The same procedure as in Example 1 was performed, except that the air gap was set at 15 cm and that the extrusion pressure was set at 4.0 MPa. The state of the extruded laminate was evaluated. The results are shown in Table 3.

Examples 11 to 14 and Comparative Examples 4 to 5

The same procedure as in Example 10 was performed, except that the extrusion pressure was set at the pressures shown in Table 3. The state of the extruded laminate was evaluated. The results are shown in Table 3.

(Evaluation Methods)

1. Selvage shaking width of the homo-PET layer
   - ○ . . . Selvage shaking width of within 2 mm
   - Δ . . . Selvage shaking width of less than 4 mm
   - x . . . Selvage shaking width of 4 mm or more The laminate with a selvage shaking width of less than 4 mm can be put to practical use.

2. Uniformity of the film thickness
   - ○ . . . The range of fluctuations in the film thickness of the homo-PET layer was within ±15% of the desired film thickness.
   - Δ . . . The range of fluctuations in the film thickness of the homo-PET layer was less than ±20% of the desired film thickness.
   - x . . . The range of fluctuations in the film thickness of the homo-PET layer was equal to or more than ±20% of the desired film thickness.

The laminate with a range of fluctuations of less than ±20% can be put to practical use.

3. Adhesion
   - ○ . . . There was sufficient adhesion between the homo-PET layer and the paper substrate.
   - Δ . . . There was adhesion between the homo-PET layer and the paper substrate.
   - x . . . In some cases, slight peeling occurred between the homo-PET layer and the paper substrate.

The laminate without peeling between the homo-PET layer and the paper substrate can be put to practical use.

4. Heat-Sealability

In connection with the laminates obtained in Examples 1 to 14 and Comparative Examples 1 to 2, the homopolyethylene terephthalate-laminated surfaces were superposed, and a heating plate adjusted to each of heat-sealing temperatures of 160° C., 170° C., 190° C. and 220° C. was held at a pressure of 2 kg/cm² for 2 seconds by an impulse sealer, to heat-seal the composite.

Then, the heat-sealed surfaces of the laminate subjected to heat sealing were stripped, and the state of breakage of the surface at the paper substrate was observed. Evaluation criteria are as follows:

◎ ... Breakage at the paper substrate surface was 90% or more of the welded area ○ ... Breakage at the paper substrate surface was 60% or more, but less than 90% of the welded area Δ ... Breakage at the paper substrate surface was 30% or more, but less than 60% of the welded area x ... Breakage at the paper substrate surface was less than 30% of the welded area The results are shown in Table 4.

TABLE 1

| | Air gap (cm) | Selvage shaking width of coated film | Uniformity of film thickness | Adhesion |
|---|---|---|---|---|
| Ex. 2 | 5 | ○ | Δ | ○ |
| Ex. 1 | 10 | ○ | ○ | ○ |
| Ex. 3 | 15 | ○ | ○ | ○ |
| Ex. 4 | 20 | ○ | ○ | ○ |
| Ex. 5 | 25 | Δ | Δ | Δ |
| Comp. Ex. 1 | 30 | X | X | Δ |

(Extrusion temperature: 300° C., Extrusion pressure: 6.0 MPa)

TABLE 2

| | Extrusion temperature (° C.) | Selvage shaking width of coated film | Uniformity of film thickness | Adhesion |
|---|---|---|---|---|
| Comp. Ex. 2 | 270 | Δ | X | Δ |
| Ex. 6 | 280 | ○ | ○ | ○ |
| Ex. 7 | 290 | ○ | ○ | ○ |
| Ex. 8 | 300 | ○ | ○ | ○ |
| Ex. 9 | 310 | Δ | Δ | ○ |
| Comp. Ex. 3 | 320 | X | X | Δ |

(Air gap: 15 cm, Extrusion pressure: 6.0 MPa)

TABLE 3

| | Pressure (MPa) | Selvage shaking width of coated film | Uniformity of film thickness | Adhesion |
|---|---|---|---|---|
| Comp. Ex. 4 | 3.5 | Δ | Δ | Δ |
| Ex. 10 | 4.0 | ○ | Δ | ○ |
| Ex. 11 | 4.5 | ○ | ○ | ○ |
| Ex. 12 | 5.0 | ○ | ○ | ○ |
| Ex. 13 | 5.5 | ○ | ○ | ○ |
| Ex. 14 | 6.0 | ○ | ○ | ○ |
| Comp. Ex. 5 | 6.5 | Δ | Δ | ○ |

(Air gap: 15 cm, Extrusion temperature: 300° C.)

TABLE 4

| | PET surface/PET surface | | | |
|---|---|---|---|---|
| | 160° C. | 170° C. | 190° C. | 220° C. |
| Ex. 1 | ◎ | ◎ | ◎ | ◎ |
| Ex. 2 | ◎ | ◎ | ◎ | ◎ |
| Ex. 3 | ◎ | ◎ | ◎ | ◎ |
| Ex. 4 | ◎ | ◎ | ◎ | ◎ |
| Ex. 5 | Δ | ○ | ◎ | ◎ |
| Ex. 6 | ◎ | ◎ | ◎ | ◎ |
| Ex. 7 | ◎ | ◎ | ◎ | ◎ |
| Ex. 8 | ◎ | ◎ | ◎ | ◎ |
| Ex. 9 | ◎ | ◎ | ◎ | ◎ |
| Ex. 10 | ◎ | ◎ | ◎ | ◎ |
| Ex. 11 | ◎ | ◎ | ◎ | ◎ |
| Ex. 12 | ◎ | ◎ | ◎ | ◎ |
| Ex. 13 | ◎ | ◎ | ◎ | ◎ |
| Ex. 14 | ◎ | ◎ | ◎ | ◎ |
| Comp. Ex. 1 | X | X | Δ | ○ |
| Comp. Ex. 2 | Δ | Δ | ○ | ◎ |

Examples 15 to 18

The homopolyethylene terephthalates used were homopolyethylene terephthalate having an inherent viscosity of 0.88 dL/g and a melting point of 250° C. (NEH-2070, produced by UNITIKA, LTD.) (Example 15), homopolyethylene terephthalate having an inherent viscosity of 0.80 dL/g and a melting point of 236° C. (BR8040, produced by SK Chemicals Co., Ltd.) (Example 16), homopolyethylene terephthalate having an inherent viscosity of 0.76 dL/g and a melting point of 252° C. (TRN-8550FF, produced by Teijin Chemicals Ltd.) (Example 17), and homopolyethylene terephthalate having an inherent viscosity of 0.72 dL/g and a melting point of 251° C. (NES-2040, produced by UNITIKA, LTD.) (Example 18). The extrusion conditions were the same as those in Example 1, except that the extrusion temperature was 290° C. only for BR8040 of SK Chemicals Under these conditions, laminates were prepared in the same manner as in Example 1, and evaluated in the same manner as in Example 1. The results are shown in Tables 5 and 6.

TABLE 5

| | Pressure | Selvage shaking width of coated film | Uniformity of film thickness | Adhesion |
|---|---|---|---|---|
| Ex. 15 | 5.0 | ○ | ○ | ○ |
| Ex. 16 | 5.0 | ○ | ○ | ○ |
| Ex. 17 | 5.0 | ○ | ○ | ○ |
| Ex. 18 | 5.0 | ○ | ○ | ○ |

TABLE 6

| | PET surface/PET surface | | | |
|---|---|---|---|---|
| | 160° C. | 170° C. | 190° C. | 220° C. |
| Ex. 15 | ◎ | ◎ | ◎ | ◎ |
| Ex. 16 | ◎ | ◎ | ◎ | ◎ |
| Ex. 17 | ◎ | ◎ | ◎ | ◎ |
| Ex. 18 | ◎ | ◎ | ◎ | ◎ |

2. Concentrating Tests of Ethanol

(1) Storage Tests Using Various Laminates

Example 19

In connection with the laminate obtained in Example 1, homopolyethylene terephthalate was laminated to the surface, to which no homopolyethylene terephthalate was laminated, so as to achieve a coating thickness of 40 μm whereby a laminate was completed. The material composition of the laminate was PET (25 μm)/paper/PET (40 μm). This laminate was cut into two rectangular pieces of A4 size (210×297 mm). With the homopolyethylene terephthalate surfaces (the 40 μm sides) being superposed, the two pieces were heat-sealed at their corresponding three edges by a heating plate (adjusted to 200° C.) at a pressure of 2 kg/cm$^2$ for 2 seconds to prepare a simple container.

The interior of the simple container was charged with an ethanol aqueous solution (about 25% (v/v)) in an amount of the order of 90 to 99 g, and then the simple container was heat-sealed at the remaining edge at 200° C. in the same manner as mentioned above, to achieve a sealed state where ethanol was sealed up in the container having the homopolyethylene terephthalate surface as the inner surface.

The laminate accommodating ethanol after the heat sealing was placed in a constant temperature bath at 60° C., and then the ethanol concentration inside the laminate was measured at 1 day, 4 days, 7 days, 14 days and 21 days. The results are shown in Table 7. The concentration is expressed as v/v %.

Comparative Example 6

As a comparative example relative to the laminate used in the present invention, a laminate having polyethylene laminated onto both surfaces of a paper substrate was used to prepare a container for sealing in an ethanol aqueous solution in the same manner as in Example 19. The material composition of the laminate was low-density PE (polyethylene) (60 μm)/paper/medium-density PE (40 μm). The resulting container, which had the medium-density PE (40 μm) surface as its inner surface, was charged with ethanol and sealed in the same manner as in Example 19 to attain a sealed state. The ethanol concentration inside the container was measured in the same manner as in Example 19. The results are shown in Table 7.

Comparative Example 7

As a comparative example relative to the laminate used in the present invention, a laminate was prepared by using a substrate having an aluminum sheet laminated to paper, and further laminating homopolyethylene terephthalate to the aluminum sheet surface by the method of Example 1. The material composition of the laminate was paper/aluminum sheet (7 μm)/PET (40 μm). A container formed from this laminate, with the PET (40 μm) surface as its inner surface, was charged with an ethanol aqueous solution and sealed in the same manner as in Example 19 to attain a sealed state. The ethanol concentration inside the container was measured in the same manner as in Example 19. The results are shown in Table 7.

Comparative Example 8

As a comparative example relative to the laminate used in the present invention, a laminate was prepared by using a polyethylene terephthalate film having aluminum vapor-deposited thereon, and further laminating homopolyethylene terephthalate to the aluminum sheet surface by the method of Example 1. The material composition of the laminate was aluminum-vapor-deposited PET (12 μm)/PET (25 μm). A container formed from this laminate, with the PET (25 μm) surface as its inner surface, was charged with an ethanol aqueous solution and sealed in the same manner as in Example 19 to attain a sealed state. The ethanol concentration inside the container was measured in the same manner as in Example 19. The results are shown in Table 7.

TABLE 7

|  | Ex. 19 Laminate of present invention | | Comp. Ex. 6 Polyethylene | | Comp. Ex. 7 Aluminum sheet | | Comp. Ex. 8 Aluminum vapor deposited PET | |
| --- | --- | --- | --- | --- | --- | --- | --- | --- |
|  | weight (g) | ethanol conc. (%) | weight (g) | ethanol conc. (%) | weight (g) | ethanol conc. (%) | weight (g) | ethanol conc. (%) |
| Day 1 | 91.8 | 26.3 | 97.0 | 23.9 | 98.8 | 24.7 | 96.8 | 24.2 |
| Day 4 | 73.4 | 32.8 | 88.0 | 24.1 | 98.6 | 24.6 | 96.9 | 25.0 |
| Day 7 | 60.3 | 39.7 | 77.1 | 23.4 | 98.8 | 24.2 | 95.6 | 25.0 |
| Day 14 | 24.3 | 69.5 | 58.9 | 22.0 | 98.1 | 23.5 | 92.3 | 25.1 |
| Day 21 | 18.9 | 94.4 | 36.0 | 22.1 | 99.1 | 24.7 | 87.9 | 27.3 |

With the alcohol concentration method of the present invention (Example 19), the alcohol concentration was initially of the order of 25%, but gradually increased, and reached 94% at 21 days. When polyethylene (Comparative Example 6), aluminum sheet (Comparative Example 7), or aluminum-vapor-deposited PET (Comparative Example 8), which had high water vapor barrier properties, was used, on the other hand, the ethanol concentration remained unchanged, and no alcohol (ethanol) concentration effect was observed.

(2) Comparison with Stretched Polyethylene Terephthalate Film

Example 20

The laminate having homopolyethylene terephthalate laminated therein, which was used in Example 19, was subjected to heat sealing to prepare a container having the homopolyethylene terephthalate surface as the inner surface. The container was charged with ethanol, and heat-sealed to attain a sealed state. The laminate container accommodating ethanol after the heat sealing was placed in a constant temperature bath at 60° C., and then the ethanol concentration inside the container was measured at 1 day, 7 days, 14 days, 21 days and 28 days. The results are shown in Table 8. The concentration is expressed as v/v %.

Comparative Example 9

A container was formed using a biaxially stretched polyethylene terephthalate film (40 μm), and ethanol was sealed inside the container in the same manner as in Example 19 to prepare an ethanol sealed-in product. The stretched polyethylene terephthalate film was not heat-sealable when subjected to a heating plate (adjusted to a temperature of 200° C.) for 2 seconds at a pressure of 2 kg/cm². Thus, the temperature was held at 250° C. for 5 seconds, whereby the film surfaces were fused and integrated to achieve the sealed state of the container where ethanol was sealed in. However, the forced integration associated with fusion caused pinholes, resulting in the leakage of ethanol from inside. At 7 days, ethanol was not measurable.

TABLE 8

|  | Ex. 20 Laminate of present invention | | Comp. Ex. 9 Stretched PET | |
| --- | --- | --- | --- | --- |
|  | weight (g) | ethanol conc. (%) | weight (g) | ethanol conc. (%) |
| Day 1 | 88.5 | 27.5 | 46.8 | 27.3 |
| Day 7 | 51.0 | 39.9 | — | — |
| Day 14 | 18.6 | 95.5 | — | — |
| Day 21 | 16.4 | 96.9 | — | — |
| Day 28 | 16.0 | 99.4 | — | — |

In connection with Example 20, the alcohol concentration was of the order of 25% initially, but became as high as 99% or higher at 28 days. This outcome proves that the alcohol concentration method according to the present invention can concentrate ethanol to a high concentration.

The stretched polyethylene terephthalate film was found to be insufficiently heat-sealable and be difficult to achieve a sealed state. Thus, this film was demonstrated to pose difficulty in finding use in alcohol concentration.

(3) Storage Tests of Various Alcohol Solutions

Guaranteed reagents of methanol, ethanol, propanol and butanol, and water were each sealed into the simple container used in Example 19, and the respective simple containers were sealed in the same manner as in Example 19, except that the heat sealing conditions were 160° C. for 1 second. Each of the sealed containers was stored in a thermostatic chamber at 60° C., and changes in the weight were checked, with the weight at the time of sealing (Day 0) as 100%. The results are shown in Table 9 and FIG. 2.

TABLE 9

|  | Package | | Water | | Methanol aqueous solution | | Ethanol aqueous solution | | Propanol aqueous solution | | Butanol aqueous solution | |
| --- | --- | --- | --- | --- | --- | --- | --- | --- | --- | --- | --- | --- |
|  | weight (g) | (%) | weight (g) | (%) | weight (g) | (%) | weight (g) | (%) | weight (g) | (%) | weight (g) | (%) |
| Day 0 | 20.7 | 100.0 | 100.6 | 100.0 | 100.6 | 100.0 | 100.6 | 100.0 | 100.7 | 100.0 | 100.6 | 100.0 |
| Day 1 | 20.7 | 100.0 | 92.6 | 92.1 | 94.6 | 94.0 | 98.7 | 98.1 | 98.6 | 97.9 | 100.6 | 100.0 |
| Day 2 | 20.7 | 100.0 | 85.5 | 85.0 | 87.5 | 87.0 | 96.9 | 96.3 | 96.9 | 96.2 | 99.9 | 99.3 |
| Day 5 | 20.8 | 100.0 | 65.1 | 64.7 | 76.3 | 75.8 | 91.4 | 90.8 | 92.7 | 92.0 | 98.0 | 97.4 |
| Day 6 | 20.8 | 100.0 | 58.4 | 58.1 | 71.7 | 71.3 | 89.5 | 89.0 | 91.2 | 90.5 | 97.2 | 96.6 |
| Day 7 | 20.7 | 100.0 | 51.3 | 51.0 | 71.2 | 70.8 | 87.9 | 87.4 | 89.5 | 88.8 | 96.6 | 96.0 |
| Day 8 | 20.7 | 100.0 | 44.5 | 44.2 | 66.5 | 66.1 | 86.2 | 85.7 | 87.4 | 86.7 | 95.8 | 95.2 |
| Day 9 | 20.8 | 100.0 | 37.7 | 37.5 | 62.5 | 62.1 | 85.1 | 84.6 | 85.6 | 84.9 | 95.1 | 94.5 |
| Day 12 | 20.7 | 100.0 | 18.4 | 18.3 | 49.5 | 49.2 | 81.3 | 80.8 | 83.2 | 82.5 | 92.8 | 92.2 |
| Day 13 | 20.8 | 100.0 | 12.4 | 12.3 | 45.3 | 45.0 | 80.3 | 79.8 | 82.1 | 81.5 | 92.1 | 91.5 |
| Day 14 | 20.7 | 100.0 | 6.8 | 6.6 | 40.4 | 40.2 | 78.9 | 78.4 | 80.8 | 80.2 | 90.8 | 90.2 |
| Day 15 | 20.7 | 100.0 | 3.5 | 3.5 | 35.5 | 35.3 | 77.4 | 77.0 | 79.6 | 79.0 | 90.5 | 89.9 |

Figure 2:
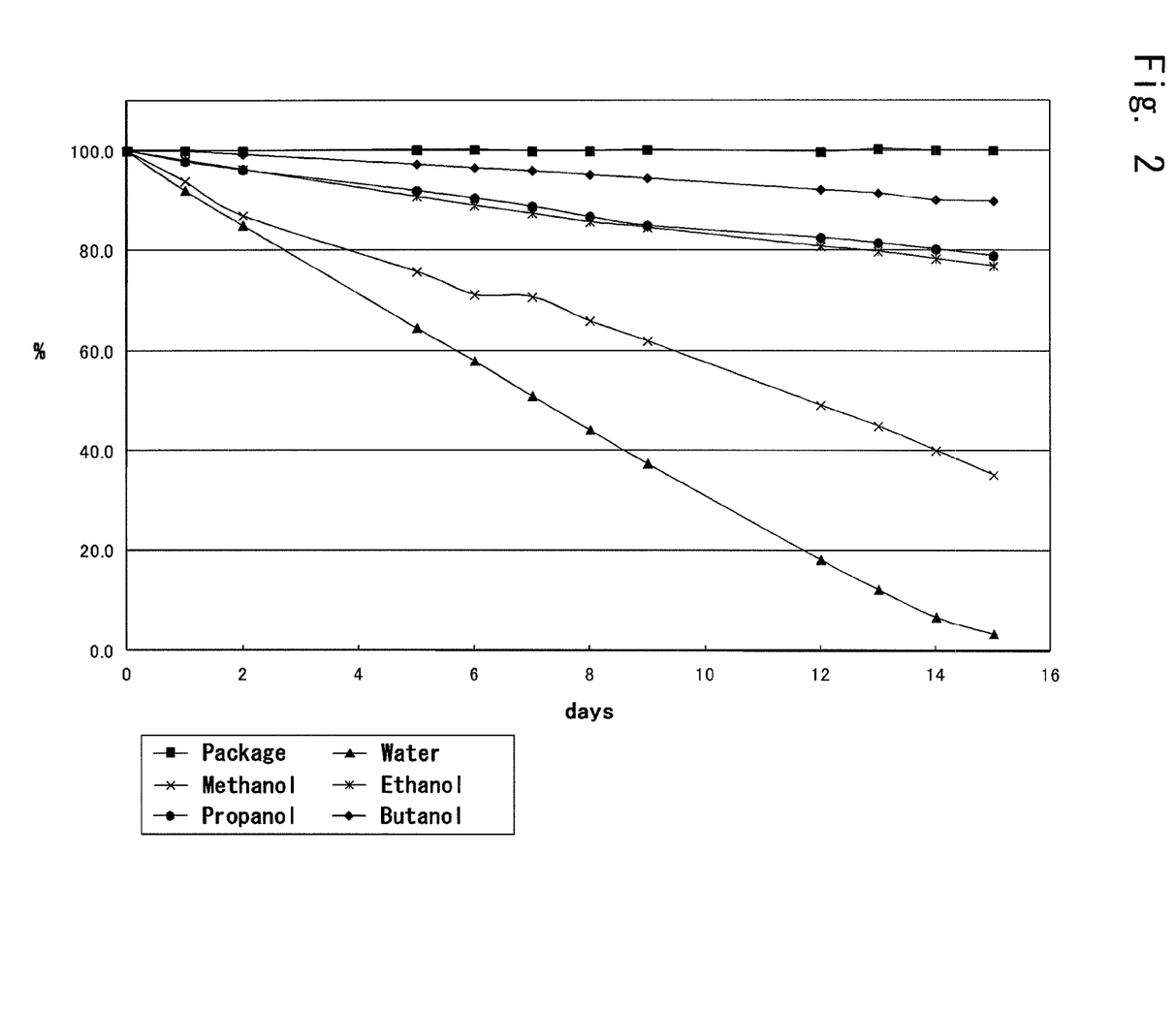
FIG. 2 is a view showing weight changes in storage tests of aqueous solutions of various alcohols.

As shown in Table 9 and FIG. 2, weight decreases were clearly smaller when the various alcohols were sealed in than in the simple containers having only water sealed in. The degree of the weight decrease was different depending on the type of the alcohol, but it was found that the alcohol itself volatilized minimally from the simple container, while water rapidly volatilized.

(4) Storage Tests of Alcohol Aqueous Solutions Containing Impurities

Six materials, i.e., 50.7 g of water (Sample 1), 52.1 g of 99.5% ethanol (Sample 2), 10.2 g of sodium chloride (Sample 3), 101.3 g of an alcohol aqueous solution containing a 1:1 (volume ratio) mixture of 99.9% ethanol and water (Sample 4), 51.4 g of a 25% aqueous solution of sodium chloride (Sample 5), and 101.7 g of an alcohol aqueous solution containing a 1:1 (volume ratio) mixture of a 25% aqueous solution of sodium chloride and 99.9% ethanol (Sample 6), were each sealed into the simple container used in Example 19. The respective simple containers were sealed in the same manner as in Example 19, except that the heat sealing conditions were 160° C. for 1 second. Each of the sealed containers was stored in a thermostatic chamber at 60° C., and changes in the weight were checked. The results are shown in Table 10 and FIG. 3.

TABLE 10

| Day | Sample 1 water weight (g) | Sample 2 ethanol weight (g) | Sample 3 sodium chloride weight (g) | Sample 4 ethanol + water weight (g) | Sample 5 water + sodium chloride weight (g) | Sample 6 water + sodium chloride + ethanol weight (g) |
|---|---|---|---|---|---|---|
| 0 | 50.7 | 52.0 | 10.2 | 101.3 | 54.4 | 101.7 |
| 1 | 46.0 | 51.9 | 10.2 | 96.0 | 48.4 | 97.3 |
| 2 | 40.9 | 51.3 | 10.1 | 90.6 | 45.2 | 92.4 |
| 5 | 27.9 | 50.3 | 10.3 | 78.5 | 37.9 | 82.0 |
| 6 | 23.0 | 49.6 | 10.1 | 74.0 | 35.3 | 78.4 |
| 7 | 18.2 | 49.3 | 10.1 | 68.2 | 33.1 | 74.9 |
| 8 | 13.0 | 48.9 | 10.2 | 66.2 | 30.7 | 71.7 |
| 9 | 7.8 | 48.4 | 10.1 | 62.6 | 28.5 | 68.9 |
| 12 | 0.0 | 47.3 | 10.1 | 54.4 | 20.9 | 63.0 |
| 13 | −0.1 | 46.8 | 10.1 | 52.0 | 17.2 | 61.3 |
| 14 | 0.0 | 46.6 | 10.1 | 50.8 | 14.8 | 60.4 |
| 15 | 0.0 | 46.4 | 10.3 | 49.9 | 12.5 | 59.7 |
| 19 | 0.0 | 45.0 | 10.2 | 47.6 | 10.1 | 57.1 |
| 20 | 0.0 | 44.5 | 10.1 | 47.3 | 10.1 | 56.6 |
| 21 | 0.1 | 44.1 | 10.1 | 46.9 | 10.1 | 56.0 |
| 22 | 0.1 | 43.7 | 10.1 | 46.6 | 10.1 | 55.6 |

Figure 3:
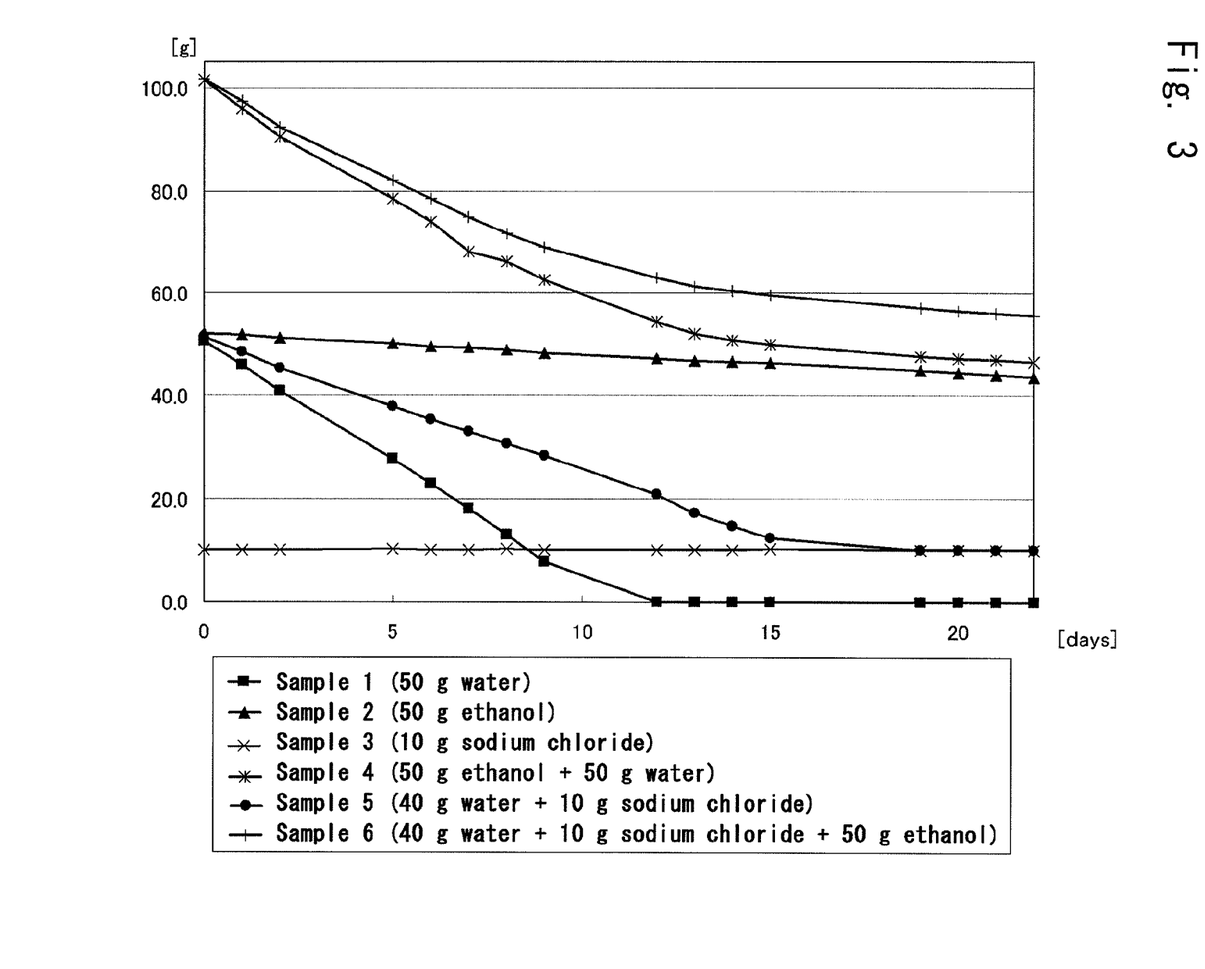
FIG. 3 is a view showing weight changes in storage tests of alcohol aqueous solutions containing impurities.

As shown in Table 10 and FIG. 3, the impurities (sodium chloride)-containing alcohol aqueous solution (Sample 6) decreased in the weight to nearly the same degree as the impurities-free alcohol aqueous solution (Sample 4) after the passage of time, when the amount of the precipitated impurities (sodium chloride) was excluded. This finding proved that alcohol was concentrated as in the impurities-free alcohol aqueous solution.

INDUSTRIAL APPLICABILITY

The alcohol concentration method of the present invention can concentrate an alcohol aqueous solution with ease, at a low cost and with high efficiency. This method can be utilized effectively for concentration to a high concentration alcohol usable for alcohol fuels.

EXPLANATIONS OF LETTERS OR NUMERALS

1 Die, 2 Die lip, 3 Chill roll, 4 Pressure roll
The invention claimed is:
1. An alcohol concentration method, including following steps of:
sealing in an alcohol-containing aqueous solution by a laminate formed by extrusion lamination of polyethylene terephthalate onto at least one surface of an air permeable film-shaped substrate; and
storing the alcohol-containing aqueous solution in the laminate for a predetermined period of time.

2. The alcohol concentration method according to claim 1, wherein the polyethylene terephthalate is homopolyethylene terephthalate.

3. The alcohol concentration method according to claim 1, wherein the laminated surface in the laminate formed by extrusion lamination of the polyethylene terephthalate is heat sealable.

4. The alcohol concentration method according to claim 1, wherein the substrate is paper or a nonwoven fabric.

5. The alcohol concentration method according to claim 1, wherein an inherent viscosity of the polyethylene terephthalate is 0.72 to 0.88 dL/g.

6. The alcohol concentration method according to claim 1, wherein the extrusion lamination is performed by a laminating method which comprises extruding molten polyethylene terephthalate through a die for lamination, wherein an air gap ranging from an opening of the die to the supporting substrate is 25 cm or less.

* * * * *